(12) United States Patent
Komoschinski et al.

(10) Patent No.: US 6,964,963 B2
(45) Date of Patent: Nov. 15, 2005

(54) PREPARATION OF 4-AMINO-1-NAPHTHOL ETHERS

(75) Inventors: Joachim Komoschinski, Köln (DE); Herbert Diehl, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 186 days.

(21) Appl. No.: 10/228,529

(22) Filed: Aug. 27, 2002

(65) Prior Publication Data

US 2003/0083525 A1 May 1, 2003

(30) Foreign Application Priority Data

Aug. 31, 2001 (DE) ......................................... 101 42 461
Nov. 2, 2001 (DE) ......................................... 101 54 076

(51) Int. Cl.$^7$ .................... A61K 31/535; A61K 31/497; A61K 31/16
(52) U.S. Cl. .............................. 514/239.2; 514/252.12; 514/628; 514/629; 544/165; 544/400; 564/221; 564/223
(58) Field of Search ........................ 514/239.2, 252.12, 514/628, 629; 544/165, 400; 564/221, 223

(56) References Cited

U.S. PATENT DOCUMENTS

| 3,933,913 A | * | 1/1976 | Colella et al. | ............... | 564/365 |
| 3,947,446 A | * | 3/1976 | Witte et al. | ................. | 544/394 |
| 4,178,442 A | * | 12/1979 | Bourgery et al. | ........... | 540/596 |

FOREIGN PATENT DOCUMENTS

| DE | 827951 | 1/1952 |
| WO | 94/01394 | 1/1994 |
| WO | 00/43384 | 7/2000 |

OTHER PUBLICATIONS

Imperial Chemical Industries Ltd. Chem. Abst. 65:7099b–g (1966).*

J. Org. Chem., 11, (month unavailable) 1946, pp. 454–462, G. Bryant Bachman and John W. Wetzel, "Compounds of Pharmaceutical Interest From 4–Methoxy–1–Naphthylamine".

J. Org. Chem., 17, (month unavailable) 1952, pp. 693–697, Robert M. Herbst and Philip Johnson, "The Synthesis of Some Tertiary Naphthoxyethylamines".

Cablewski, T. et al.: "A new, regioselective, tandem amidation reaction of electron–rich arenes".

Yokoyama, M. et al.: "Local anesthetics. II. Synthesis of the 1–alkoxynaphthylamine derivatives." Yakugaku Zasshi, Bd. 78, 1958, Seiten 428–431, XP009002770 Seite 428; Tabelle I.

Hach, V. et al.: "Local anesthetics. V. Alkoxy derivatives of xylocaine analogues." Chem. Listy, Bd. 50, 1956, Seiten 952–960, XP001121095 Seite 953; Beispiel VIB Seite 957, Absatz 3.

Patent Abstracts of Japan vol. 1999, No. 12, Oct. 29, 1999 & JP 11 180966 A (Sankyo Co Ltd), Jul. 6, 1999 Zusammenfassung Seite 27; Beispiel 7.12 RN 230634–32–9.

* cited by examiner

Primary Examiner—Peter O'Sullivan
(74) Attorney, Agent, or Firm—Diderico van Eyl

(57) ABSTRACT

The present invention describes a process for preparing 4-amino-1-naphthol ethers which is characterized in that naphthol ethers are first prepared from 1-naphthols, the former are then converted to the corresponding 4-acetamino-1-naphthol ethers and then the acyl group is cleaved off, and further describes 4-acetamino-1-naphthol ethers obtained thereby.

5 Claims, No Drawings

PREPARATION OF 4-AMINO-1-NAPHTHOL ETHERS

BACKGROUND OF THE INVENTION

1. Field of the Invention

The present invention relates to a process for preparing 4-amino-1-naphthol ethers and novel intermediates.

2. Brief Description of the Prior Art

4-Amino-1-naphthol ethers are valuable intermediates in preparing active pharmaceutical ingredients (see, for example, WO 00/43384; B. Bachman, J. Wetzel, J. Org. Chem., 11,1946, p. 454–462; R. Herbst, P. Johnson, J. Org. Chem., 17, 1952, p. 693–697). The synthetic route disclosed, for example, by WO 00/43384 starts from 4-amino-1-naphthol hydrochloride and comprises the conversion of the amine to a protected derivative, the alkylation of the hydroxy group and then the cleavage of the protecting group. This process has the disadvantage that both the reactant and the protecting group reagents used are very expensive and the conversion to the desired 4-amino-1-naphthol ethers still requires three steps. The synthesis of 4-amino-1-methoxynaphtalene according to B. Bachman, J. Wetzel, J. Org. Chem., 11, 1946, p. 454–462 is similar and accordingly has the same disadvantages.

There is accordingly a need to develop an efficient process which, starting from inexpensive 1-naphthols, facilitates the preparation of 4-amino-1-naphthol ethers in a few steps.

SUMMARY OF THE INVENTION

A process for preparing 4-amino-1-naphthol ethers has now been found that is characterized in that
a) substituted or unsubstituted 1-naphthols are reacted with reactive alkyl compounds optionally in the presence of a base, to give 1-naphthol ethers,
b) the 1-naphthol ethers are then converted to the corresponding 4-acylamino-1-naphthol ethers using hydroxylammonium salts and carboxylic acids and
c) these 4-acylamino-1-naphthol ethers are converted to the free 4-amino-1-naphthol ethers or analogous ammonium salts by acidic or basic acyl group cleavage.

DETAILED DESCRIPTION OF THE INVENTION

Preference is given to using the substituted or unsubstituted 1-naphthols of the general formula (I) for step a) of the process according to the invention

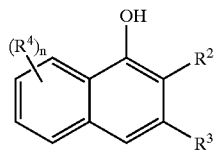

(I)

where
$R^2$ is hydrogen, halogen or $C_1$–$C_4$-alkyl and
$R^3$ is hydrogen, halogen, $C_1$–$C_4$-alkyl or $C_1$–$C_4$-alkoxy and
n is zero, one, two, three or four and
$R^4$ are each independently halogen, nitro, cyano, protected formyl, $C_1$–$C_8$-alkyl, $C_7$–$C_{10}$-arylalkyl, $C_1$–$C_8$-hydroxyalkyl, $C_1$–$C_8$-haloalkyl or $C_6$–$C_{10}$-aryl or substituents of the general formula (II), $$D\text{-}E\text{-}F \qquad (II)$$

where, independently,
D is absent or is a $C_1$–$C_8$-alkylene radical and
E is a carbonyl group or sulphonyl group and
F is $R^6$, $OR^6$, $NH_2$, $SR^6$, $NHR^6$ or $NR^6R^7$,
where
$R^6$ and $R^7$ are each independently substituted or unsubstituted $C_1$–$C_8$-alkyl, $C_1$–$C_8$-haloalkyl, $C_7$–$C_{12}$-arylalkyl or $C_6$–$C_{10}$-aryl or
$NR^6R^7$ together is a 5- to 8-membered heterocycle.

Alkyl or alkylene in the context mentioned are each independently a straight-chain, cyclic, branched or unbranched alkyl or alkylene radical. The same applies to the alkyl moiety of an arylalkyl radical.

Examples of $C_1$–$C_4$-alkyl radicals include methyl, ethyl, n-propyl, isopropyl and n-butyl, and for $C_1$–$C_8$-alkyl radicals also n-pentyl, n-hexyl, cyclohexyl, n-heptyl, n-octyl and isooctyl.

Examples of $C_1$–$C_8$-alkylene radicals include methylene, 1,1-ethylene, 1,2-ethylene, 1,2-propylene, 1,3-propylene, 1,4-butylene and 1,2-cyclohexylene.

Examples of $C_7$–$C_{12}$-arylalkyl radicals include benzyl and p-methylbenzyl.

Examples of $C_1$–$C_4$-alkoxy radicals include methoxy, ethoxy, n-propoxy, isopropoxy and n-butoxy.

The term aryl refers both to carbocyclic and heteroaromatic radicals in which none, one, two or three skeletal carbon atoms per cycle, but at least one skeletal carbon atom in the entire radical, is substituted by heteroatoms selected from the group consisting of nitrogen, sulphur and oxygen. The carbocyclic aromatic radicals or heteroaromatic radicals may further be substituted by up to five identical or different substituents per cycle selected from the group consisting of bromine, chlorine, fluorine, nitro, cyano, free or protected formyl, $C_1$–$C_8$-alkyl, $C_1$–$C_8$-hydroxyalkyl and radicals as defined for the general formula (II).

Carbocyclic, aromatic radicals or heteroaromatic radicals may be, for example, substituted or unsubstituted phenyl, pyridyl, imidazolyl or pyrazolyl.

The same applies to the aryl moiety of an arylalkyl radical.

Halogen in the context mentioned is fluorine, chlorine, bromine or iodine.

Haloalkyl in the context mentioned is independently a straight-chain, cyclic, branched or unbranched alkyl radical which is substituted by one, more than one or completely by halogen atoms selected independently from the group consisting of fluorine, chlorine and bromine.

Examples of $C_1$–$C_8$-haloalkyl radicals include trifluoromethyl, pentafluoroethyl, 2,2,2-trifluoroethyl, trichloromethyl and 2-chloroethyl.

Each hydroxyalkyl in the context mentioned is independently a straight-chain, cyclic, branched or unbranched alkyl radical which is substituted by one or more hydroxyl groups in such a way that each carbon atom of the radical bears not more than one oxygen, sulphur or nitrogen atom.

Examples of $C_1$–$C_8$-hydroxyalkyl radicals include hydroxymethyl and 2-hydroxyethyl.

Protected formyl is a formyl radical which is protected by conversion to aminal, acetal or a mixed aminalacetal, and the aminals, acetals and mixed aminalacetals may be acyclic or cyclic.

A 5- to 8-membered heterocycle is a heterocycle which, as well as a nitrogen, also contains up to 3 further heteroatoms selected from the group consisting of nitrogen, oxygen and sulphur.

Examples of such heterocycles include unsubstituted or substituted pyrrolidines, piperidines or morpholines.

Particular preference is given to using substituted or unsubstituted 1-naphthols of the general formula (I) in step a) of the process according to the invention where
$R^2$ is hydrogen and
$R^3$ is hydrogen and
n is zero, one or two and
$R^4$ are each independently halogen, nitro, cyano, $C_1$–$C_8$-alkyl, $C_1$–C8-haloalkyl or substituents of the general formula (III),
where, independently,
D is absent and
E is a carbonyl group or sulphonyl group and
F is $R^6$, $OR^6$, $NH_2$, $NHR^6$ or $NR^6R^7$ and where
$R^6$ and $R^7$ are each independently substituted or unsubstituted $C_1$–$C_4$-alkyl.

Very particular preference is given to using 1-naphthol in step a).

The substituted or unsubstituted 1-naphthols are reacted in step a) with reactive alkyl compounds to give 1-naphthol ethers, optionally in the presence of a base.

Examples of reactive alkyl compounds include compounds of the general formula (IIIa) or (IIIb),

$$R^1\text{—}Y \quad (\text{IIIa})$$

$$(R^1\text{—O})_2SO_2 \quad (\text{IIIb})$$

where, for example,
$R^1$ is $C_3$–$C_{12}$-alkyl, $C_2$–$C_8$-haloalkyl, $C_7$–$C_{13}$-arylalkyl or substituents of the general formula (IV),

$$A\text{-}B \quad (\text{IV})$$

where
A is $C_2$–$C_8$-alkylene, $C_2$–$C_8$-haloalkylene and
B is $NR^6R^7$, $SR^6$ or $OR^6$
where
$R^6$ and $R^7$ are each independently substituted or unsubstituted $C_1$–$C_8$-alkyl, $C_1$–$C_8$-haloalkyl, $C_7$–$C_{12}$-arylalkyl or $C_6$–$C_{10}$-aryl or
$NR^6R^7$ together is a 5- to 8-membered heterocycle and
Y is chlorine, bromine, iodine or sulphonate.
Particular preference is given to using activated alkyl compounds of the general formula (IIIa) where
$R^1$ is a substituent of the general formula (IV) where
A is $C_2$–$C_4$-alkylene or $C_2$–$C_4$-haloalkylene and
B is $NR^6R^7$or $OR^6$ and
where
$R^6$ and $R^7$ are each independently substituted or unsubstituted $C_1$–$C_4$-alkyl or
$NR^6R^7$ together is a 5- or 6-membered heterocycle and
Y is chlorine, bromine, iodine, methanesulphonate, tosylate or trifluoromethanesulphonate.

Very particular preference is given to using activated alkyl compounds of the general formula (IIIa) where
$R^1$ is a substituent of the general formula (IV) where
A is 1,2-ethylene and
B is $NR^6R^7$ or $OR^6$,
where
$R^6$ and $R^7$ are each independently substituted or unsubstituted $C_1$–$C_4$-alkyl or
$NR^6R^7$ together is pyrrolidinyl, piperidinyl or morpholinyl and
Y is chlorine, bromine or trifluoromethanesulphonate.

Greatest preference is given to N-(2-chloroethyl) morpholine, N-(2-bromoethyl)morpholine, N-(2-methanesulphonylethyl)morpholine, and even greater preference to N-(2-chloroethyl)morpholine.

Preference is given to using the compounds of the general formulae (IIIa) and (IIIb) when they contain an amine nitrogen in the form of their ammonium salts.

For example, N-(2-chloroethyl)morpholine is preferably used in the form of a hydrochloride.

The compounds of the general formulae (IIIa) or (IIIb) may be used, for example, in a molar ratio of from 0.8 to 2.0, based on the substituted or unsubstituted 1-naphthol used, and preference is given to a ratio of from 0.9 to 1.5, even greater preference to a ratio of from 1.0 to 1.4.

The conversion of substituted or unsubstituted 1-naphthols to the 1-naphthol ethers may be carried out, for example, in the presence of base in a suitable solvent at a suitable temperature.

Examples of useful bases include hydroxides, alkoxides, hydrides, amides, carbonates and hydrogen carbonates of alkali metals or alkaline earth metals or amines.

Preference is given to the hydroxides or carbonates of the alkali metals, more preference to sodium hydroxide, potassium hydroxide, sodium carbonate or potassium carbonate. Very particular preference is given to sodium hydroxide.

Preference is given to using alkali metal hydroxides in the form of an aqueous solution having a base content of from 30 to 70% by weight, greater preference to a solution of from 30 to 70% by weight of sodium hydroxide in water.

The base quantity may be, for example, from 0.8 to 5.0 equivalents, based on the substituted or unsubstituted 1-naphthol used, preference is given to from 0.9 to 1.5 equivalents, even greater preference to from 0.9 to 1.2 equivalents.

When, for example, compounds of the general formulae (IIIa) or (IIIb) having amine nitrogen are used in the form of their ammonium salts, the base quantity has to be increased by a corresponding molar quantity.

Examples of useful solvents for step a) of the process according to the invention include aliphatic or aromatic hydrocarbons, such as , toluene, xylene or hexane, chlorinated hydrocarbons, such as, chlorobenzene or methylene chloride, ethers, such as, tetrahydrofuran or diethyl ether, alcohols, such as, methanol, ethanol or isopropanol, esters, such as ethyl acetate, or polar aprotic solvents, such as, dimethylformamide or dimethyl sulphoxide, or mixtures of such solvents. Preference is given to carrying out the reaction in an alcohol.

A very particularly preferred solvent for step a) is ethanol.

The temperature for step a) may, for example, be from 0 to 120° C., preferably from 20 to 80° C., more preferably from 40 to 80° C.

The pressure during the reaction is preferably ambient pressure.

In a preferred embodiment of step a), for example, the substituted or unsubstituted 1-naphthol and the reactive alkyl compound, for example N-(2-chloroethyl)morpholinyl hydrochloride, is initially charged in ethanol and sodium hydroxide is added as a 30–70% aqueous solution at from 40 to 60° C.

In the manner according to the invention, 1-naphthol ethers, for example, of the general formula (V) are obtained,

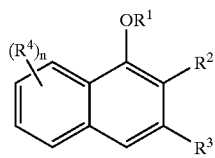

(V)

where

R$^1$, R$^2$, R$^3$, R$^4$ and n are as defined above with the areas of preference mentioned.

The acylamination of the electron-rich aromatics, for example a 1-methoxynaphtalene, is disclosed by T. Cablewski et al., J. Org. Chem., 1994, 59, p. 5814–5817, but the process described there is only slightly regioselective.

According to the invention, step b), the conversion of the 1-naphthol ethers to 4-acylamino-1-naphthol ethers may, for example, be carried out in such a way, that the 1-naphthol ethers are reacted with a hydroxylammonium salt and a carboxylic acid in the presence of polyphosphoric acid.

For the purposes of the present invention, polyphosphoric acid refers to such polyphosphoric acids which have a content of over 100%, based on orthophosphoric acid.

Preference is given to a content of from 100% to 300%, more preferably from 100% to 150%. Very particular preference is given to commercial polyphosphoric acid having a content of 116%, based on orthophosphoric acid.

The quantity of the polyphosphoric acid used may, for example, be from 5 to 12 times, preferably from 5 to 8 times, the molar quantity of the unsubstituted or substituted 1-naphthol ether. The molar quantity of polyphosphoric acid reported is based on the content of orthophosphoric acid.

Examples of useful hydroxylammonium salts include hydroxylamine hydrochloride, hydroxylamine hydrogensulphate and hydroxylamine dihydrogenphosphate. Preference is given to hydroxylamine hydrochloride.

Examples of useful carboxylic acids include those of the general formula (VI)

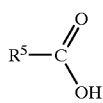

(VI)

where

R$^5$ is C$_1$–C$_6$-alkyl or C$_1$–C$_4$-haloalkyl or anhydrides thereof.

Preference is given to acetic acid, trifluoroacetic acid, propionic acid and anhydrides thereof, and particular preference is given to acetic acid, propionic acid and trifluoroacetic acid. Even greater preference is given to acetic acid.

The quantity of the carboxylic acid of the general formula (VI) used may, for example, be from 0.8 to 20 times the molar quantity of the unsubstituted or substituted 1-naphthol ether used, preferably from 1.0 to 3.0 times, more preferably from 1.2 to 1.5 times.

The temperature during the reaction may, for example, be from 50 to 130° C., preferably from 70 to 120° C.

The overall reaction duration may, for example, be from 1 to 48 hours, preferably from 2 to 10 hours, more preferably from 5 to 8 hours.

In a preferred embodiment of step b), carboxylic acid, hydroxylammonium salt and polyphosphoric acid are initially charged and the 1-naphthol ether is metered in at a temperature of from 70 to 90° C. over a period of from 0.5 to 8 hours, preferably from 1 to 5 hours and more preferably from 2 to 4 hours, and then heated at 100–120° C. for a period of from 1 to 10 hours, preferably from 1 to 4 hours.

Preference is given to effecting the workup in such a way that the reaction mixture is brought into contact with ice and, optionally after addition of water, the pH is adjusted using a base, preferably sodium hydroxide, to from 9 to 10. Preference is given to holding the temperature below 40° C., more preferably at or below 25° C.

In the manner according to the invention, for example, 4-acylamino-1-naphthol ethers of the general formula (VIIa) are obtained,

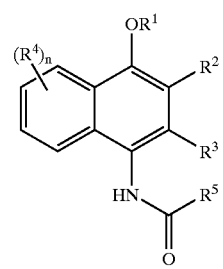

(VIIa)

where

R$^1$ is C$_3$–C$_{12}$-alkyl, C$_2$–C$_8$-haloalkyl, C$_7$–C$_{13}$-arylalkyl or substituents of the general formula (IV),

A-B  (IV)

where

A is C$_2$–C$_8$-alkylene, C$_2$–C$_8$-haloalkylene and

B is NR$^6$R$^7$, SR$^6$ or OR$^6$, where

R$^6$ and R$^7$ are each independently substituted or unsubstituted C$_1$–C8-alkyl, C$_1$–C$_8$-haloalkyl, C$_7$–C$_{12}$-arylalkyl or C$_6$–C$_{10}$-aryl or NR$^6$R$^7$ together is a 5- to 8-membered heterocycle and R$^2$ is hydrogen, halogen or C$_1$–C$_4$-alkyl and R$^3$ is hydrogen, halogen, C$_1$–C$_4$-alkyl or C$_1$–C$_4$-alkoxy and n is zero, one, two, three or four and R$^4$ are each independently halogen, nitro, cyano, protected formyl, C$_1$–C$_8$-alkyl, C$_7$–C$_{10}$-arylalkyl, C$_1$–C$_8$-hydroxyalkyl, C$_1$–C$_8$-haloalkyl or C$_6$–C$_{10}$-aryl or substituents of the general formula (II)

D-E-F  (II)

where, independently,

D is absent or is a C$_1$–C$_8$-alkylene radical and

E is a carbonyl group or sulphonyl group and

F is R$^6$, OR$^6$, NH$_2$, SR$^6$, NHR$^6$ or NR$^6$R$^7$, and where
$R^6$ and $R^7$ are each independently substituted or unsubstituted $C_1$–$C_8$-alkyl, $C_1$–$C_8$-haloalkyl, $C_7$–$C_{12}$-arylalkyl or $C_6$–$C_{10}$-aryl or
$NR^6R^7$ together is a 5- to 8-membered heterocycle and
$R^5$ is $C_1$–$C_6$-alkyl or $C_1$–$C_4$-haloalkyl.

The compounds of the general formula (VIIa) are likewise part of the subject-matter of the invention. Examples of individual compounds include 4-(2-([1]-naphthyloxy-[4]-acetamino)ethyl)morpholine, 4-(2-([1]-naphthyloxy-[4]-propionylamino)ethyl)morpholine and 4-(2-([1]-naphthyloxy-[4]-trifluoroacetamino)ethyl)morpholine.

The compounds of the general formula (VIIa) may either be stored or reacted further. Preference is given to further reactions. If the compounds of the general formula (VIIa) are to be stored and $R^1$ also contains amine nitrogen, the compounds can also be converted to the analogous ammonium compounds. For example, 4-(2-([1]-naphthyloxy-[4]-acetamino)ethyl)morpholine, 4-(2-([1]-naphthyloxy-[4]-propionylamino)ethyl)morpholine and 4-(2-([1]-naphthyloxy-[4]-trifluoro-acetamino)ethyl)morpholine can be converted to the corresponding morpholinium salts by reacting the compounds, optionally in a solvent, with an equivalent of an acid, H-An.

The compounds of the general formula (VIIb) accordingly also form part of the subject-matter of the invention

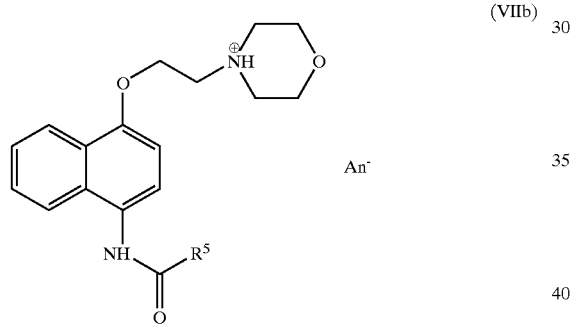

(VIIb)

where
$R^5$ is a $C_1$–$C_6$-alkyl or $C_1$–$C_4$-haloalkyl radical
and An⁻
is the anion of an acid.

Preferred H-An acids include mineral acids, for example, sulphuric acid, hydrochloric acid, hydrobromic acid, phosphoric acid or tetrafluoroboric acid, hydrogen halides, for example, hydrogen chloride or hydrogen bromide, carboxylic acids such as those of the general formula (VI), where $R^5$ is as defined above, or sulphonic acids, for example methanesulphonic acid. The anions, An derive correspondingly from the H-An acids.

The 4-acylamino-1-naphthol ethers may be converted to the corresponding 4-amino-1-naphthol ethers according to step c). This step may be effected in a manner similar to the literature (for example, B. Bachman, J. Wetzel, J. Org. Chem., 11, 1946, p. 454–462), for example, by acidic or alkaline acyl group cleavage, and preference is given to hydrolysis used in an acid, which converts the 4-amino-1-naphthol ethers to the form of ammonium salts. When $R^1$ radicals which contain amine nitrogen are used, the 4-amino-1-naphthol ether occur in the form of the diammonium salts.

Examples of useful acids include those which have a pKa of 2 or less. Examples thereof include hydrogen halides such as hydrogen chloride, hydrogen bromide or hydrogen iodide, mineral acids, for example, hydrochloric acid, hydrobromic acid, sulphuric and/or phosphoric acid, or organic sulphonic acids, such as methanesulphonic acid, or mixtures of such acids.

Preference is given to hydrochloric acid and sulphuric acid, very particular preference to concentrated hydrochloric acid.

In the manner according to the invention, step c) gives 4-amino-1-naphthol ethers of the general formula (VIIIa) or the ammonium salts thereof of the general formula (VIIIb)

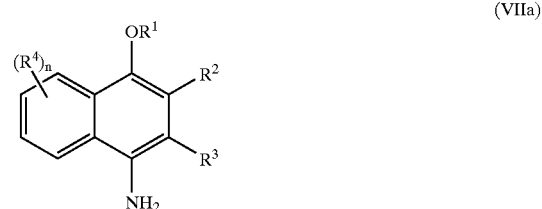

(VIIa)

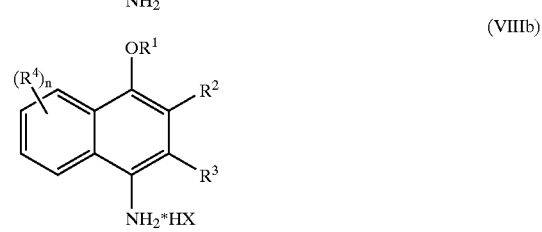

(VIIIb)

where
$R^1$, $R^2$, $R^3$, $R^4$ and n are as defined for formula (VIIa) and
X is the anion of an acid.
If the $R^1$ radical contains amine nitrogen, the formula (VIIIb) also includes the ammonium salts thereof.

An example of an individual compound is 4-(2-([1]-naphthyloxy-[4]-amino)ethyl)morpholine dihydrochloride.

The compounds of the general formulae (VIIa), (VIIb), (VIIIa) and (VIIIb) are suitable in particular for use in a process for preparing pharmaceuticals.

The process according to the invention is in particular notable in that it uses the inexpensive 1-naphthols as starting substances and leads selectively in a few steps to the desired 4-amino-1-naphthol ethers or ammonium salts thereof in high yields.

The invention is further illustrated but is not intended to be limited by the following examples in which all parts and percentages are by weight unless otherwise specified.

EXAMPLES

Example 1

Preparation of 4-(2-([1]-naphthyloxy)ethyl)morpholine 441 g of 1-naphthol and 648 g of N-(2-chloroethyl)morpholine hydrochloride are initially charged in 2680 ml of ethanol at 50° C. 554 g of 50% aqueous sodium hydroxide are added dropwise within 3 h. Stirring is then continued at 50° C. for 3 h and then for 1 h under reflux.

The salt formed is filtered off and washed with ethanol. The combined filtrates are concentrated on a rotary evaporator "to dryness" at 80° C. in a bath and 10 mbar. The cooled residue is dissolved in 1200 ml of diethyl ether and extracted first with 180 ml of water, then twice with 450 ml of 5% aqueous sodium hydroxide each time and finally twice with 150 ml of water each time. The ether phase is dried over sodium sulphate and concentrated at 60° C. and 10 mbar to dryness.

Yield: 741 g 4-(2-([1]-naphthyloxy)ethyl)morpholine in a purity of 97.7% (GC). This corresponds to 93.8% of theory, based on 1-naphthol.

Example 2

Preparation of 4-(2-([1]-naphthyloxy-[4]-acetamido)ethyl) morpholine 376 g of glacial acid and 224 g of hydroxylammonium chloride are initially charged in 2090 g of polyphosphoric acid at 80° C. in a stirred flask. 830 g of 4-(2-([1]-naphthyloxy)ethyl)morpholine are metered in with good stirring within 3 h. During the metering in, the temperature should not exceed 90° C. Stirring is then continued first at 80–90° C. for 1 h and then at 115° C. for a further 3 h.

The reaction mixture is allowed to cool to 80° C. and stirred with 1800 g of ice. The temperature is allowed to fall to 30–35° C. After addition of 9.75 l of water, precipitation is effected using 50% aqueous sodium hydroxide (2005 g) to a pH of 4–5. During the precipitation, the temperature should not exceed 25° C. Stirring is continued for 30 min and the precipitate is then filtered off. The resulting filtercake is washed with a little water.

The filtercake is suspended in 10 l of water and is dissolved with heating to 90° C. The solution is clarified using activated carbon. 530 g of 50% aqueous sodium hydroxide is added with stirring in 1 h until a pH of 10 is obtained. The resulting crystal suspension is filtered off at 50° C. and the resulting filtercake washed to neutrality with a lot of water. The filtercake is then dried in a vacuum drying cabinet.

Weight: 846 g of 4-(2-([1]-naphthyloxy-[4]-acetamido) ethyl)morpholine in a purity of 99.3% (HPLC). This corresponds to 85.1% of theory, reckoned on 4-(2-([1]-naphthyloxy)ethyl)morpholine

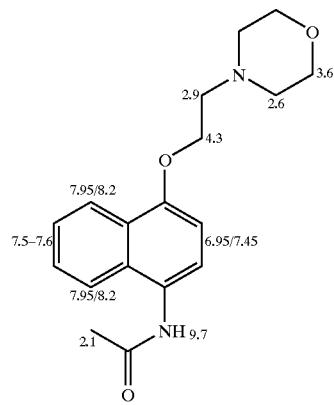

NMR data in ppm (400 MHz); solvent: DMSO

Elemental analysis:

| | | | | | |
|---|---|---|---|---|---|
| Theoretical: | C = 68.77% | H = 7.05% | N = 8.91% |
| Found: | C = 68.65% | H = 6.9% | N = 8.8% |

Example 3

4-(2-([1]-Naphthyloxy-[4]-amino)ethyl)morpholine Dihydrochloride 846 g of 4-[2-([1]-naphthyloxy-[4]-acetamido)ethyl] morpholine are suspended in 1340 ml of water and stirred with 2470 g of 37% hydrochloric acid. Hydrolysis is then effected at 95° C. for 5 h. At the end of the reaction time, 1600 g of isopropanol are added and the suspension is cooled with stirring. The resulting crystals are filtered off and washed with 4530 g of isopropanol until the filtrate is substantially colourless. Recrystallization is then effected from ethanol and the product dried in a vacuum drying cabinet.

Yield: 839 g of 4-(2-([1]-naphthyloxy-[4]-amino)ethyl) morpholine dihydrochloride.

Example 4

Preparation of the Free 4-(2-([1]-naphthyloxy-[4]-amino) ethyl)morpholine 839 g of the dihydrochloride from Example 3 are dissolved in 5600 ml of water. In a beaker, 450 ml of water are adjusted to pH 12 using 50% aqueous sodium hydroxide. After seed crystals are created in the aqueous sodium hydroxide initial charge, 50% aqueous sodium hydroxide is simultaneously added dropwise to the remaining solution in such a way that the pH of 10–12 is maintained. 390 g of 50% aqueous sodium hydroxide are used. The resulting crystals are filtered off and washed with 3300 ml of water until the filtrate has a pH of 8. The filtercake is then dried in the vacuum drying cabinet.

The yield of free amine is virtually quantitative (620 g) in a purity of 99.4% (HPLC).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. 4-Acylamino-1-naphthol ethers of the general formula (VIIa)

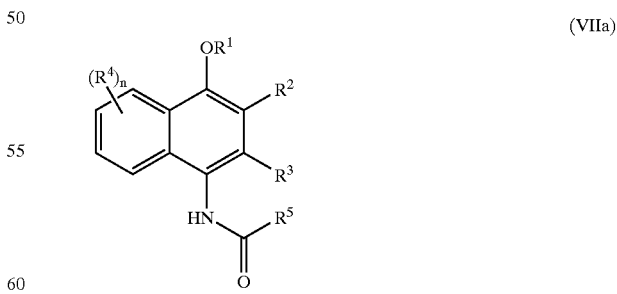

where $R^1$ is $C_3$–$C_{12}$-alkyl, $C_2$–$C_8$-haloalkyl, $C_7$–$C_{13}$-arylalkyl or substituents of the general formula (IV)

A-B (IV)

where

A is $C_2$–$C_8$-alkylene, $C_2$–$C_8$-haloalkylene and

B is $NR^6R^7$, $SR^6$ or $OR^6$ where $R^6$ and $R^7$ are each independently substituted or unsubstituted $C_1$–$C_8$-alkyl, $C_1$–$C_8$-haloalkyl, $C_7$–$C_{12}$-arylalkyl or $C_6$–$C_{10}$-aryl or $NR^6R^7$ together is a 5- to 8-membered heterocycle and $R^2$ is hydrogen, halogen or $C_1$–$C_4$-alkyl and $R^3$ is hydrogen, halogen, $C_1$–$C_4$-alkyl or $C_1$–$C_4$-alkoxy and n is zero, one, two, three or four and $R^4$ are each independently halogen, nitro, cyano, protected formyl, $C_1$–$C_8$-alkyl, $C_7$–$C_{10}$-arylalkyl, $C_1$–$C_8$-hydroxyalkyl, $C_1$–$C_8$-haloalkyl or $C_6$–$C_{10}$-aryl or substituents of the general formula (II)

D-E-F      (II)

where, independently,

D is absent or is a $C_1$–$C_8$-alkylene radical and

E is a carbonyl group or sulphonyl group and

F is $R^6$, $OR^6$, $NH_2$, $SR^6$, $NHR^6$ or $NR^6R^7$ and where $R^6$ and $R^7$ are each independently substituted or unsubstituted $C_1$–$C_8$-alkyl, $C_1$–$C_8$-haloalkyl, $C_7$–$C_{12}$-arylalkyl or $C_6$–$C_{10}$-aryl or $NR^6R^7$ together is a 5- to 8-membered heterocycle and $R^5$ is $C_1$–$C_6$-alkyl or $C_1$–$C_4$-haloalkyl.

2. 4-(2-([1]-naphthyloxy-[4]-acetamino)ethyl)morpholine.

3. 4-(2-([1]-naphthyloxy-[4]-propionylamino)ethyl)morpholine.

4. 4-(2-([1]-naphthyloxy-[4]-trifluoroacetamino)ethyl)morpholine.

5. Compounds of the general formula (VIIb)

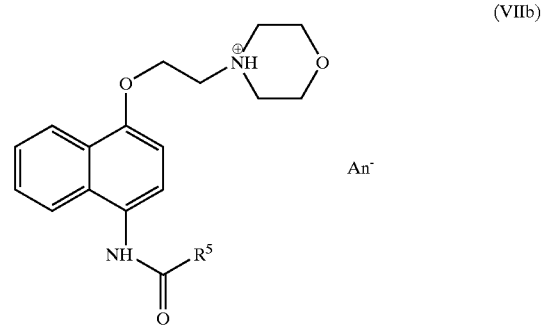

(VIIb)

where $R^5$ is a $C_1$–$C_6$-alkyl or $C_1$–$C_4$-haloalkyl radical and

An– is the anion of an acid.

* * * * *